US009814864B2

(12) United States Patent
Scarpine et al.

(10) Patent No.: US 9,814,864 B2
(45) Date of Patent: Nov. 14, 2017

(54) TORQUE APPARATUS FOR USE WITH A GUIDEWIRE

(71) Applicant: Covidien LP, Mansfield, MA (US)

(72) Inventors: Frank Scarpine, Brea, CA (US); Lawrence Craig Burns, Anaheim, CA (US)

(73) Assignee: Covidien LP, Mansfield, MA (US)

( * ) Notice: Subject to any disclaimer, the term of this patent is extended or adjusted under 35 U.S.C. 154(b) by 674 days.

(21) Appl. No.: 13/896,360

(22) Filed: May 17, 2013

(65) Prior Publication Data

US 2014/0343527 A1 Nov. 20, 2014

(51) Int. Cl.
*A61M 25/09* (2006.01)

(52) U.S. Cl.
CPC ............. *A61M 25/09041* (2013.01); *A61M 2025/09116* (2013.01); *A61M 2025/09125* (2013.01)

(58) Field of Classification Search
CPC ............. A61M 25/09041; A61M 2025/09116
See application file for complete search history.

(56) References Cited

U.S. PATENT DOCUMENTS

| | | | |
|---|---|---|---|
| 3,533,439 A | 10/1970 | Hall | |
| 3,847,140 A * | 11/1974 | Ayella | A61M 25/09041 600/585 |
| 4,102,074 A | 7/1978 | Andre | |
| 4,463,928 A | 8/1984 | Ueda | |
| 4,726,369 A | 2/1988 | Mar | |
| 4,786,028 A | 11/1988 | Hammond | |
| 4,854,325 A * | 8/1989 | Stevens | A61B 17/22012 600/434 |
| 4,919,389 A | 4/1990 | Hoekwater et al. | |

(Continued)

FOREIGN PATENT DOCUMENTS

| | | | |
|---|---|---|---|
| WO | 9204861 A1 | 4/1992 | |
| WO | WO 2008049088 A2 * | 4/2008 | ...... A61M 25/09041 |
| WO | 2010045373 A1 | 4/2010 | |

OTHER PUBLICATIONS

International Search Report and Written Opinion from counterpart International Application No. PCT/US2014/034267, dated Jul. 4, 2014, 13 pp.

(Continued)

*Primary Examiner* — Sean Dougherty
(74) *Attorney, Agent, or Firm* — Mark Kertz

(57) ABSTRACT

A torque apparatus for facilitating manipulation of a guidewire includes a handle member dimensioned for engagement by a clinician and defining a longitudinal axis and a torque member mounted to the handle member. The torque member defines a lumen configured for reception and passage of a guidewire and is configured to rotate relative to the handle member to impart rotational movement to the guidewire. A gripper member associated with the torque member is adapted to releasably secure the guidewire relative to the torque member and a trigger member depending from the handle member is actuable to cause the gripper member to release the guidewire to thereby permit the guidewire to be moved within the lumen of the torque member. An actuator is operatively coupled to the torque member and is movable to impart rotational movement to the torque member to thereby cause corresponding rotational movement of the guidewire.

20 Claims, 11 Drawing Sheets

(56) References Cited

U.S. PATENT DOCUMENTS

| | | | |
|---|---|---|---|
| 4,957,117 A * | 9/1990 | Wysham | A61B 17/22 600/585 |
| 4,974,811 A | 12/1990 | Ishida | |
| 5,055,109 A * | 10/1991 | Gould | A61M 25/104 600/434 |
| 5,137,288 A | 8/1992 | Starkey et al. | |
| 5,161,534 A | 11/1992 | Berthiaume | |
| 5,243,997 A * | 9/1993 | Uflacker | A61B 17/22012 600/585 |
| 5,259,587 A | 11/1993 | D'Alessio et al. | |
| 5,312,338 A | 5/1994 | Nelson et al. | |
| 5,325,746 A | 7/1994 | Anderson | |
| 5,325,868 A | 7/1994 | Kimmelstiel | |
| 5,392,778 A | 2/1995 | Horzewski | |
| 5,441,497 A | 8/1995 | Narciso, Jr. | |
| 5,443,078 A * | 8/1995 | Uflacker | A61B 17/22012 600/585 |
| 5,524,180 A * | 6/1996 | Wang | A61B 19/22 600/117 |
| 5,524,635 A * | 6/1996 | Uflacker | A61B 17/22012 600/585 |
| 5,634,475 A * | 6/1997 | Wolvek | A61M 25/09041 600/585 |
| 5,634,478 A | 6/1997 | Shakir | |
| 5,660,180 A * | 8/1997 | Malinowski | A61B 8/12 600/439 |
| 5,709,661 A * | 1/1998 | Van Egmond | A61B 1/00147 33/512 |
| 5,735,535 A * | 4/1998 | McCombs | A61B 17/162 279/131 |
| 5,851,189 A | 12/1998 | Forber | |
| 5,893,857 A * | 4/1999 | Shturman | A61B 17/32075 606/159 |
| 5,908,395 A * | 6/1999 | Stalker | A61M 25/09041 600/585 |
| 5,911,722 A * | 6/1999 | Adler | A61B 17/1624 174/170 |
| 6,027,460 A * | 2/2000 | Shturman | A61M 25/0133 600/129 |
| 6,030,349 A | 2/2000 | Wilson et al. | |
| 6,033,414 A | 3/2000 | Tockman et al. | |
| 6,042,562 A | 3/2000 | Amor | |
| 6,059,484 A | 5/2000 | Greive | |
| 6,129,330 A | 10/2000 | Guala | |
| 6,141,896 A | 11/2000 | Oberst | |
| 6,145,351 A | 11/2000 | Levenson | |
| 6,165,188 A * | 12/2000 | Saadat | A61B 17/3207 604/22 |
| 6,183,432 B1 * | 2/2001 | Milo | A61B 17/22012 604/22 |
| 6,371,571 B1 | 4/2002 | Tsan | |
| 6,533,772 B1 | 3/2003 | Sherts et al. | |
| 6,726,675 B1 * | 4/2004 | Beyar | A61M 25/0105 600/106 |
| 6,752,800 B1 * | 6/2004 | Winston | A61M 25/09041 604/157 |
| 6,949,104 B2 | 9/2005 | Griffis et al. | |
| 7,615,032 B2 | 11/2009 | Whittaker et al. | |
| 7,615,042 B2 * | 11/2009 | Beyar | A61M 25/0113 600/106 |
| 7,717,865 B2 | 5/2010 | Boutillette et al. | |
| 7,722,628 B2 | 5/2010 | Stokes et al. | |
| 7,892,186 B2 | 2/2011 | Soukup et al. | |
| 7,972,282 B2 | 7/2011 | Clark et al. | |
| 8,038,628 B2 | 10/2011 | von Malmborg et al. | |
| 8,123,763 B2 | 2/2012 | Lampropoulos et al. | |
| 8,142,458 B2 * | 3/2012 | Shturman | A61B 17/32075 606/159 |
| 8,147,481 B2 | 4/2012 | Whittaker et al. | |
| 8,500,697 B2 * | 8/2013 | Kurth | A61M 25/09 600/585 |
| 2002/0177789 A1 * | 11/2002 | Ferry | A61B 1/00147 600/585 |
| 2003/0088187 A1 * | 5/2003 | Saadat | A61B 5/015 600/547 |
| 2005/0240120 A1 * | 10/2005 | Modesitt | A61M 25/09041 600/585 |
| 2005/0244521 A1 * | 11/2005 | Strickland | A23L 1/2205 424/751 |
| 2005/0277851 A1 * | 12/2005 | Whittaker | A61M 25/0158 600/585 |
| 2006/0041245 A1 * | 2/2006 | Ferry | A61B 1/00133 604/510 |
| 2006/0074442 A1 * | 4/2006 | Noriega | A61B 17/32002 606/159 |
| 2006/0184186 A1 * | 8/2006 | Noone | A61B 17/32002 606/159 |
| 2006/0282150 A1 * | 12/2006 | Olson | A61F 2/966 623/1.11 |
| 2007/0016105 A1 * | 1/2007 | Mamourian | A61M 25/09041 600/585 |
| 2007/0060879 A1 * | 3/2007 | Weitzner | A61B 17/12045 604/95.04 |
| 2007/0219467 A1 * | 9/2007 | Clark | A61M 25/0113 600/585 |
| 2007/0225615 A1 * | 9/2007 | Chechelski | A61B 17/32075 600/585 |
| 2007/0270755 A1 * | 11/2007 | Von Oepen | A61M 25/09041 604/164.13 |
| 2008/0097465 A1 * | 4/2008 | Rollins | A61M 25/09041 606/108 |
| 2008/0108911 A1 | 5/2008 | Palmer et al. | |
| 2009/0082722 A1 * | 3/2009 | Munger | A61M 25/09041 604/95.01 |
| 2010/0204613 A1 * | 8/2010 | Rollins | A61M 25/09041 600/585 |
| 2015/0173838 A1 * | 6/2015 | Murphy | A61B 19/2203 606/130 |

OTHER PUBLICATIONS

International Preliminary Report on Patentability from counterpart International Application No. PCT/US2014/034267, dated Nov. 17, 2015, 8 pp.

\* cited by examiner

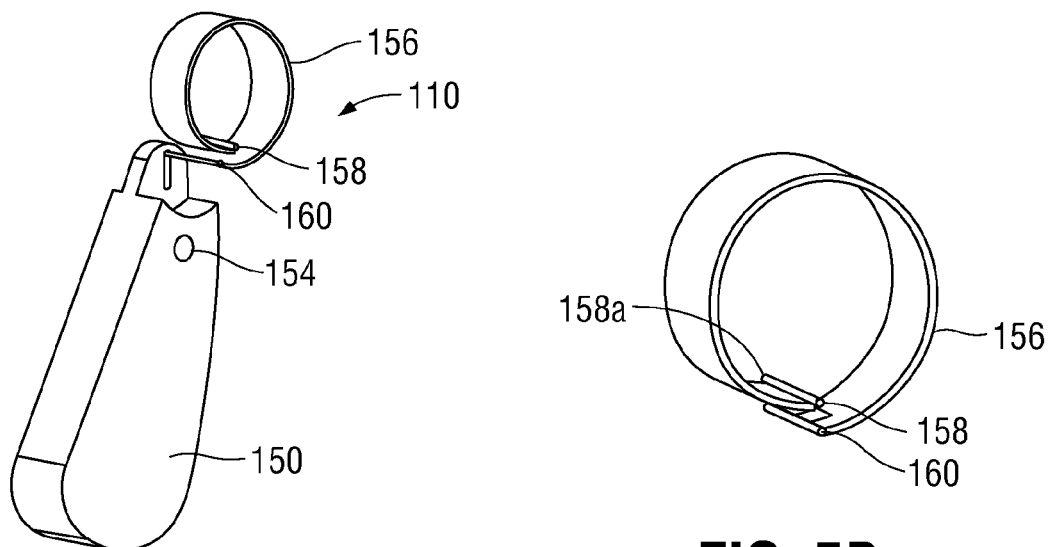
FIG. 5A
FIG. 5B
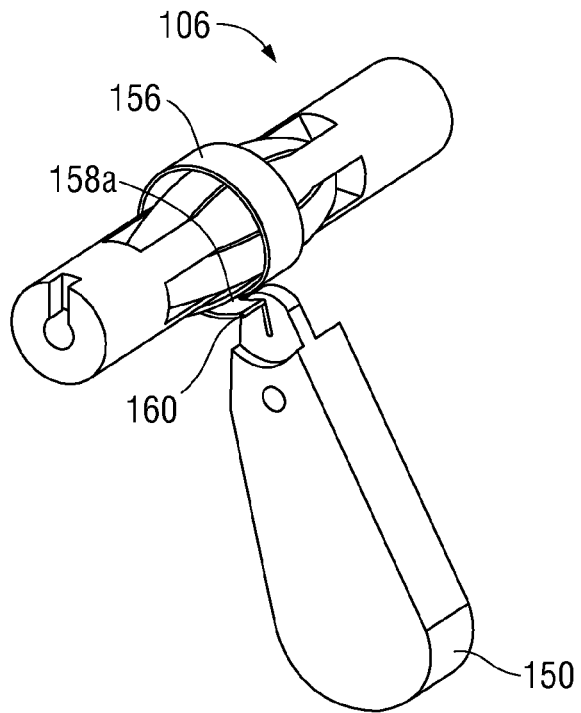
FIG. 6A

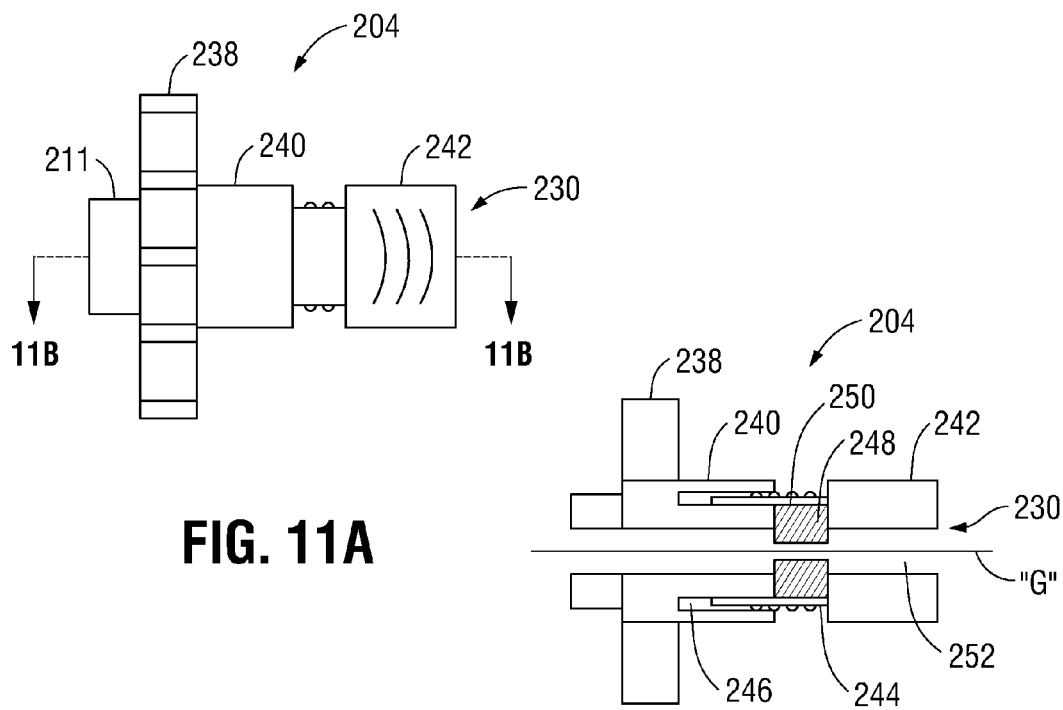
FIG. 11A
FIG. 11B
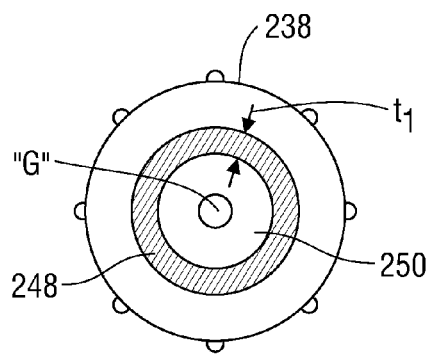
FIG. 12A
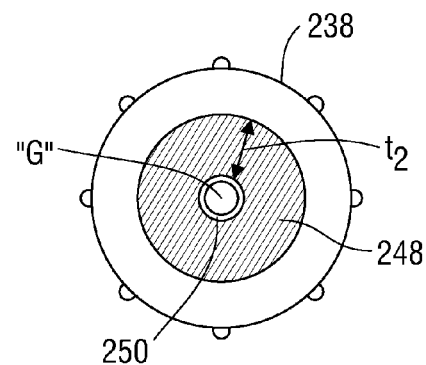
FIG. 12B

TORQUE APPARATUS FOR USE WITH A GUIDEWIRE

BACKGROUND

1. Technical Field

The present disclosure generally relates to a torque apparatus, and, in particular, relates to a torque apparatus for gripping a guidewire to facilitate maneuvering of the guidewire during an intravascular procedure.

2. Description of Related Art

Guidewires are commonly used for a variety of intravascular procedures to guide a catheter to a desired location within the body. In order to position the guidewire at the desired location, a clinician manipulates the guidewire by advancing and torquing the guidewire. Torquing the guidewire changes the orientation of the guidewire tip allowing a clinician to navigate the guidewire through the tortuous vascular system.

Guidewires may have a hydrophilic coating to provide lubricity to permit the guidewire to pass more easily through a blood vessel. However, due to the lubricity, sufficient torque cannot be applied by simply rolling or twisting the proximal end of the guidewire by the clinician. Consequently, a torque apparatus is needed to grip the guidewire for adequate torque application. Torque apparatus are well known in the art, however the majority of such apparatus require a two-handed operation in order for the clinician to reposition the torque apparatus along the guidewire. Specifically, when the clinician needs to reposition the torque apparatus along the guidewire, the user grasps one end of the torque apparatus while actuating a mechanism to release the guidewire with the other hand. The torque apparatus is then moved along the guidewire to reposition the torque device along the guidewire. As a result of the two-handed operation required to release the guidewire and reposition the torque apparatus, another clinician is needed to hold the guidewire steady while the torque device is repositioned.

SUMMARY

Accordingly, the present disclosure is directed to a torque apparatus for manipulation of a guidewire. The torque apparatus includes a handle member dimensioned for engagement by a clinician and defining a longitudinal axis and a torque member mounted to the handle member and defining a lumen configured for reception and passage of a guidewire. The torque member is configured to rotate relative to the handle member to impart rotational movement to the guidewire. A gripper member associated with the torque member is adapted to releasably secure the guidewire relative to the torque member. A trigger member depending from the handle member is actuable to cause the gripper member to release the guidewire to thereby permit the guidewire to move through the lumen of the torque member. The torque apparatus further includes a manual actuator which is operatively coupled to the torque member and is movable to impart rotational movement to the torque member to thereby cause corresponding rotational movement of the guidewire.

In disclosed embodiments, the torque apparatus also includes a counter member associated with the torque member. The counter member is dimensioned and adapted to count and/or tally incremental movements of the torque member in the clockwise or counter clockwise direction.

In disclosed embodiments, the gripper member is movable between a first engaged position in engagement with the guidewire to substantially prevent movement of the guidewire through the lumen of the torque member and to operatively couple the guidewire to the torque member whereby rotational movement of the torque member causes corresponding rotational movement of the guidewire, and a second release position released from the guidewire to permit movement of the guidewire through the lumen. The gripper member may be normally biased to the first engaged position.

In disclosed embodiments, the torque member is adapted to rotate about the longitudinal axis. The trigger member may be adapted for pivotal movement relative to the handle member between an initial position corresponding to the first engaged position of the gripper member and a pivoted position corresponding to the second release position of the gripper member. The trigger member may be normally biased to the initial position.

In disclosed embodiments, the torque member includes a shaft defining a shaft lumen therethrough for reception of the guidewire and the gripper member includes at least one spring member mounted to the shaft. The at least one spring member is arranged to engage the guidewire in general secured frictional relation therewith when the gripper member is the first engaged position and arranged to release the guidewire when the gripper member is in the second release position. The torque apparatus may include a plurality of spring members extending in a general longitudinal direction with respect to the longitudinal axis.

In disclosed embodiments, the handle member defines a substantially pistol grip arrangement.

Another aspect of the present disclosure is directed to another embodiment of the torque apparatus for facilitating manipulation of a guidewire. The torque apparatus includes a handle member dimensioned for engagement by a clinician and defining a longitudinal axis and a torque member mounted to the handle member and defining a lumen configured for reception and passage of a guidewire. The torque member is configured to rotate relative to the handle member to impart rotational movement to the guidewire. The torque member includes a gripper member associated with the torque member is adapted to releasably secure the guidewire relative to the torque member. The torque member also includes a manual actuator actuable to cause the gripper member to release the guidewire to thereby permit the guidewire to move through the lumen of the torque member. A trigger member depending from the handle member is actuable to prevent the torque member from spinning while the manual actuator is actuated to release the guidewire. The manual actuator is movable to impart rotational movement to the torque member to thereby cause corresponding rotational movement of the guidewire.

In disclosed embodiments, the torque apparatus also includes a counter member associated with the torque member. The counter member is dimensioned and adapted to count and/or tally incremental movements of the torque member.

In disclosed embodiments, the gripper member is movable between a first engaged position in engagement with the guidewire to substantially prevent movement of the guidewire through the lumen of the torque member and to operatively couple the guidewire to the torque member whereby rotational movement of the torque member causes corresponding rotational movement of the guidewire, and a second release position released from the guidewire to permit movement of the guidewire through the lumen. The gripper member may be normally biased to the second release position.

In disclosed embodiments, the torque member is adapted to rotate about the longitudinal axis. The trigger member may be adapted for pivotal movement relative to the handle member between an initial position corresponding to the first release position of the torque member and a pivoted position corresponding to the second secure position of the torque member. The trigger member may be normally biased to the initial position.

In disclosed embodiments, the handle member defines a substantially pistol grip arrangement.

In disclosed embodiments, a method for torquing a guidewire via a one handed operation of a torque apparatus is provided. In the method, a user actuates a trigger member of the torque apparatus to permit movement of a guidewire within a lumen of the torque apparatus. The trigger member being actuable by a finger on a first hand of a user. The user releases the trigger member to secure the guidewire within the lumen of the torque apparatus. The guidewire is advanced by moving the torque apparatus toward a patient. The guidewire is torqued by rotating a manual actuator of the torque apparatus. The manual actuator being rotatable by a thumb on the first hand of the user. To reposition the guidewire, the user actuates the trigger member to release the guidewire and permit movement of the guidewire within the lumen. The trigger member is released to secure the guidewire within the lumen of the torque apparatus.

The torque apparatus described herein permit a clinician to reposition a torque device along a guidewire using a one-handed operation. The guidewire is torqued independently of manipulating the handle thereby enabling a clinician to maintain the handle stationary on a flat surface for support while torquing the guidewire. Additionally, the torque apparatus allow a clinician to easily judge the torque applied to the guidewire through the use of visual indicators. The pistol grip arrangement of the torque apparatus has an ergonomic design to minimize physical effort and discomfort. Further, the pistol grip arrangement is intuitive thereby permitting a clinician to easily comprehend the correct operation of the torque apparatus.

BRIEF DESCRIPTION OF THE DRAWINGS

Embodiments of the present disclosure will be readily appreciated by reference to the drawings wherein:

FIG. 5A is a perspective view of a trigger member in accordance with an embodiment of the present disclosure;

FIG. 5B is a perspective view of a spring strap of FIG. 5A;

FIG. 6A is a perspective view of the torque and gripper assembly and trigger member assembly in accordance with an embodiment of the present disclosure;

FIG. 11A is a side view of a torque and gripper assembly in accordance with an embodiment of the present disclosure;

FIG. 11B is a cross-section view of the torque and gripper assembly of FIG. 11A taken along the lines 11B-11B;

FIG. 12A is a rear view of the torque and gripper assembly of FIG. 11A in a released position; and FIG. 12B is a rear view of the torque and gripper assembly of FIG. 11A in an engaged position.

DETAILED DESCRIPTION

Figure 1:
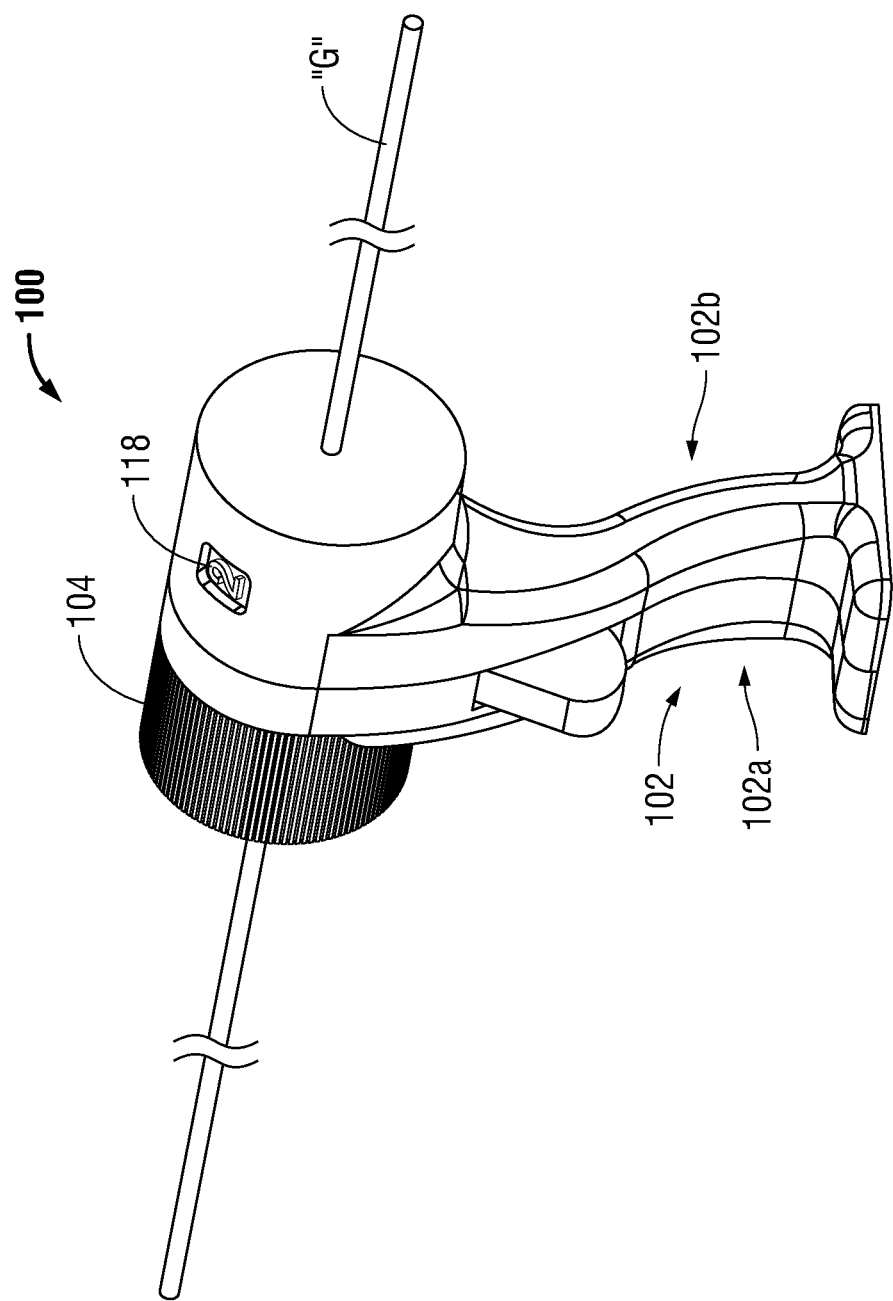
FIG. 1 is a perspective view of a torque apparatus in accordance with an embodiment of the present disclosure.

Particular embodiments of the present disclosure are described hereinbelow with reference to the accompanying drawings; however, it is to be understood that the disclosed embodiments are merely examples of the disclosure and may be embodied in various forms. Well known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure. Like reference numerals may refer to similar or identical elements throughout the description of the figures. The term "clinician" refers to any medical professional (i.e., doctor, surgeon, nurse, or the like) performing a medical procedure involving the use of embodiments described herein. As shown in the drawings and described throughout the following description, as is traditional when referring to relative positioning on a surgical instrument, the term "proximal" or "trailing" refers to the end of the apparatus which is closer to the clinician and the term "distal" or "leading" refers to the end of the apparatus which is further away from the clinician.

In the embodiments described herein, the torque apparatus is a handheld implement used to facilitate gripping and torquing of a guidewire. The torque apparatus permits a clinician to release, re-attach, and/or torque or spin a guidewire using only a single hand.

During use of the torque apparatus, the clinician grasps the torque apparatus 100 of FIG. 1 with a single hand. The clinician then actuates a trigger with his/her index finger in order to introduce a guidewire through a proximal end of the torque apparatus. The trigger is released and the guidewire is secured within the torque apparatus. Then the clinician advances the guidewire in to a vessel by moving the torque apparatus distally. While navigating the guidewire through the vessel, the clinician rotates a manual actuator with his/her thumb to orient the tip of the guidewire toward the appropriate path. When the clinician needs to reposition the torque apparatus along the guidewire to increase the length of the guidewire available to be inserted into the vessel, the clinician actuates trigger and moves the torque apparatus proximally before releasing the trigger to secure the guidewire in place. Once again, the torque apparatus is moved distally to navigate the guidewire through the vessel. This procedure is repeated until the guidewire is located in the correct position within the vessel. After the guidewire is located in the correct position, the clinician actuates trigger and moves the torque apparatus proximally over the guidewire until the guidewire is extricated.

Figure 2:
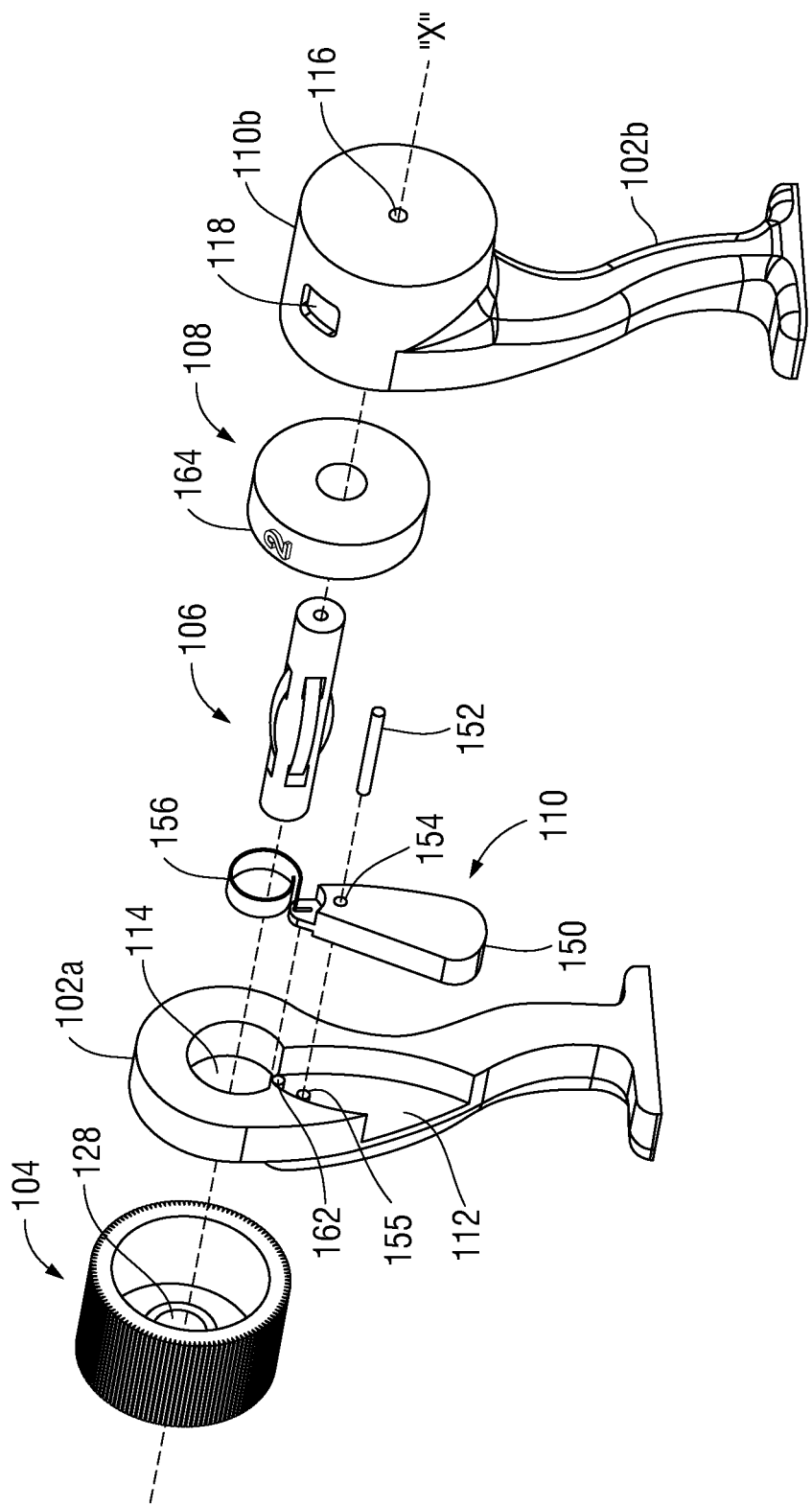
FIG. 2 is an exploded view of the torque apparatus of FIG. 1.

Referring now to FIGS. 1 and 2, the torque apparatus 100 in accordance with an embodiment of the present disclosure is illustrated. The torque apparatus 100 generally includes a handle member 102, an actuator 104 mounted to the handle member 102, a torque and gripper assembly 106 positioned within the handle member 102 and a counter member 108 also disposed within the handle member 102. The torque apparatus 100 further includes a trigger member 110 depending from the handle member 102 and couplable to the torque and gripper assembly 106. The handle member 102 may be in the form of a pistol grip and defines a longitudinal axis "X". The handle member 102 has a substantially planar lower surface dimensioned to be positioned on a support or table in the upright orientation shown in FIG. 1.

The handle member 102 may include a proximal handle segment 102a and a distal handle segment 102b which are connected to each other by conventional means. The proximal handle segment 102a defines an internal recess 112 which at least partially accommodates the trigger member 110 and a central aperture 114 in general alignment with the longitudinal axis "X". The central aperture 114 at least partially accommodates the torque and gripper assembly 106. The distal handle segment 102b includes a central aperture 116 for passage of the guidewire "G". The distal handle segment 102b may further include a window 118, which may be an opening in the wall of the distal handle segment 102b to permit viewing of the orientation of the counter member 108 as will be discussed. The proximal handle segment 102a and the distal handle segment 102b may be fabricated from any suitable material including polymeric materials formed by injection molding techniques, metallic materials such as stainless steel or any other suitable material. The handle segments 102a, 102b may be connected to each other by any conventional means such as adhesives, sonic welding techniques, and fasteners.

Figure 3:
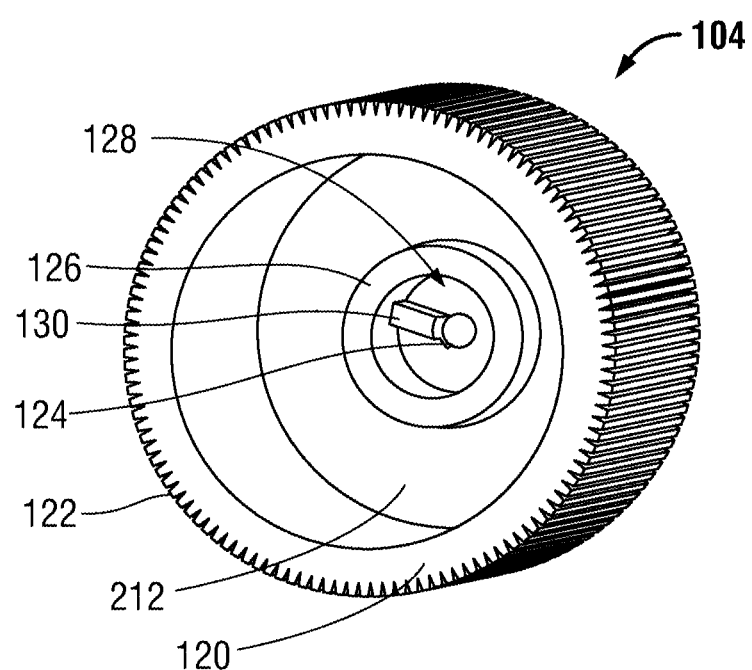
FIG. 3 is a perspective view of a manual actuator in accordance with an embodiment of the present disclosure

With reference to FIG. 3, in conjunction with FIGS. 1-2, the actuator 104 is illustrated. In the embodiments described below, the actuator 104 is shown as having a circular configuration that is manually operated. Other devices may be used to torque the torque member 132, such as, but not limited to, a crank or an electric motor. The actuator 104 may also have a smooth continuous movement or the actuator 104 may include a ratchet mechanism for incremental movements. The ratchet mechanism may provide an audible click noise to indicate the number of torques applied to the guidewire "G".

The actuator 104 is adapted for rotational movement relative to the handle member 102 about longitudinal axis "X", which effects rotation or torquing of the guidewire "G". The actuator 104 may define a general circular configuration having an outer ring 120 with a surface irregularity in the form of notches or ridges 122 to facilitate engagement and manipulation of the actuator 104 by the clinician. The actuator 104 has a central aperture 124 in general alignment with the longitudinal axis "X" to permit passage of the guidewire "G". Within the interior of the actuator 104 is an annular ring 126 coaxially disposed about the aperture 124 and defining an internal cavity 128. The internal cavity 128 is dimensioned to at least partially accommodate the torque and gripper assembly 106. A protrusion or detent 130 extends within the internal cavity 128 and is couplable with the torque and gripper assembly 106. The relationship of the detent 130 with the torque and gripper assembly 106 will be discussed in further detail hereinbelow.

Figure 4A:
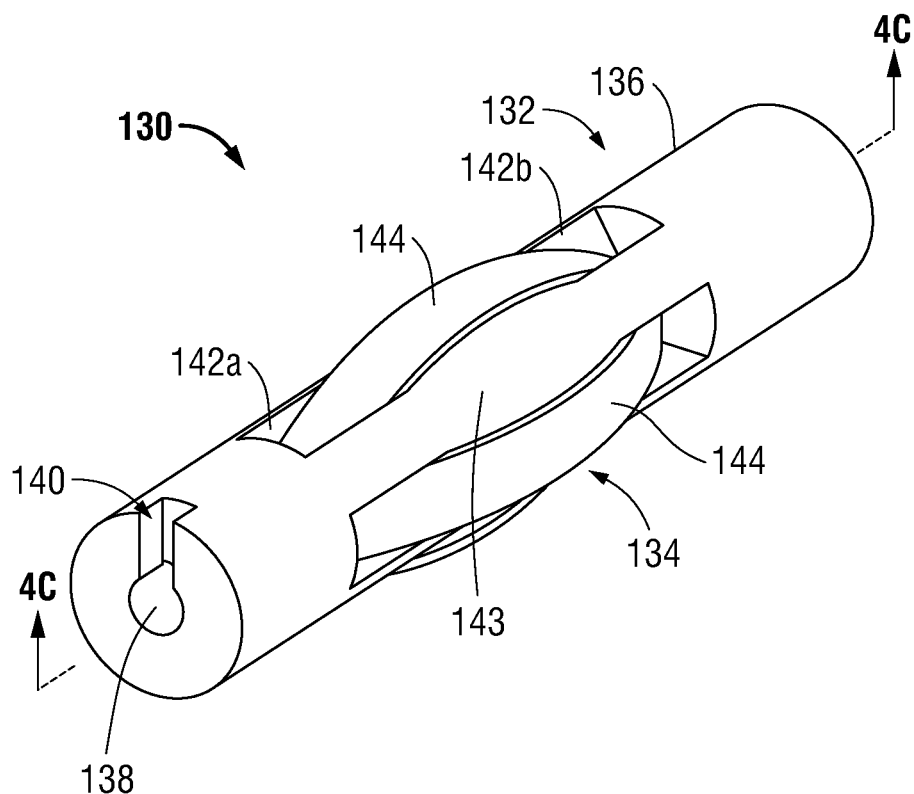
FIG. 4A is a perspective view of a torque and gripper assembly in accordance with an embodiment of the present disclosure.
Figure 4B:
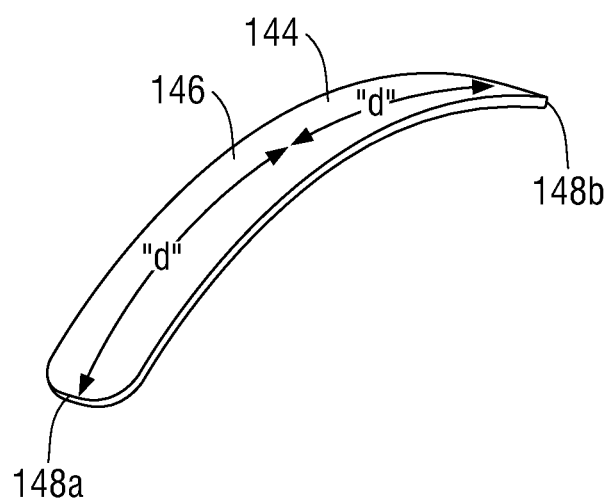
FIG. 4B is a perspective view of a leaf spring of the torque and gripper assembly in accordance with an embodiment of the present disclosure.
Figure 4C:
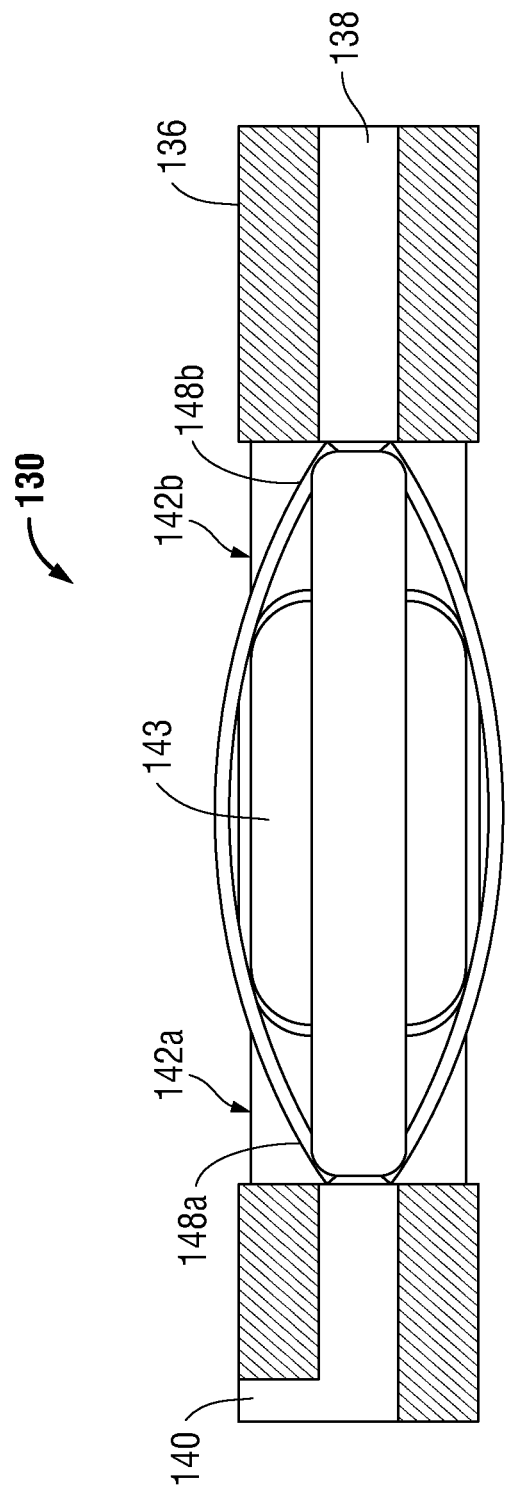
FIG. 4C is a side view of the torque and gripper assembly of FIG. 4A.

Referring now to FIGS. 4A-4C, the torque and gripper assembly 106 will be discussed. The torque and gripper assembly 106 includes a torque member 132 and a gripper member 134 couplable to the torque member 132. The torque member 132 includes a shaft 136 having or defining a lumen 138 that extends from the proximal end of the shaft 136 to the distal end of the shaft 136. The lumen 138 is aligned with longitudinal axis "X" of handle 102 and is configured to receive the guidewire "G". The torque member 132 includes a groove 140 within the shaft 136. The groove 140 is dimensioned to receive the detent 130 of the actuator 104 to couple the torque member 132 and the manual actuator 104.

The shaft 136 further includes at least one pair of apertures 142a, 142b which are spaced along the longitudinal axis "x", and separated by a central shaft segment 143. In embodiments, the shaft 136 includes four pairs of apertures 142a, 142b. The pairs of apertures 142a, 142b may be arranged equidistantly about the circumference of the shaft 136, e.g., at 90 degree intervals relative to the longitudinal axis "X".

The gripper member 134 includes at least one, and in some embodiments, four leaf springs 144. Each leaf spring 144 may be composed of a suitable resilient material such as stainless steel, a shape memory alloy, or a polymeric material. In a normal unstressed condition thereof, each leaf spring 144 defines a generally arcuate profile having a central arc segment 146 disposed between two end segments 148a, 148b. The central arc segment 146 is radially offset relative to the two end segments 148a, 148b a predetermined distance "d" (FIG. 4B). The end segments 148a, 148b of each leaf spring 144 are configured and dimensioned to be disposed in the apertures 142a and 142b, respectively, of the shaft 136 with the central arc segment 146 straddling the central shaft segment 143 of the shaft 136 as best depicted in FIG. 4C. Further details of the leaf springs 144 and their functioning in gripping and releasing the guidewire "g" will be discussed in greater detail hereinbelow.

Referring now to FIGS. 5A and 5B, in conjunction with FIG. 2, the trigger member 110 will be discussed. The trigger member 110 includes a lever 150 which is pivotally mounted to the proximal handle segment 102a about pivot pin 152. In some embodiments, pivot pin 152 is inserted into aperture 154 of lever 150 and aperture 155 of proximal handle segment 102a to mount lever 150 to proximal handle segment 102a. The lever 150 is fabricated from any suitable material including polymeric materials formed by any conventional material processing techniques. The trigger member 110 further includes a resilient strap 156 having a first end 158 couplable to the proximal handle segment 102a. The lever 150 is coupled to a second end 160 of the resilient strap 156. The resilient strap 156 has a generally circular configuration and may be fabricated from stainless steel, a shape memory alloy, or a polymeric material. Actuation through pivotal movement of the lever 150 from an initial position to a pivoted position about the pivot pin 152 causes the resilient strap 156 to transition from a first larger diameter to a second smaller diameter. For example, as a clinician actuates the lever 150, the lever 150 pivots about the pin 152 causing the second end 160 to move radially away from the longitudinal axis "X" while the first end 158 remains secured to the proximal handle segment 102a. This action causes the effective circumference of the resilient strap 156 to decrease. Upon release of the lever 150, the resilient strap 156 returns to the first larger diameter.

Figure 6B:
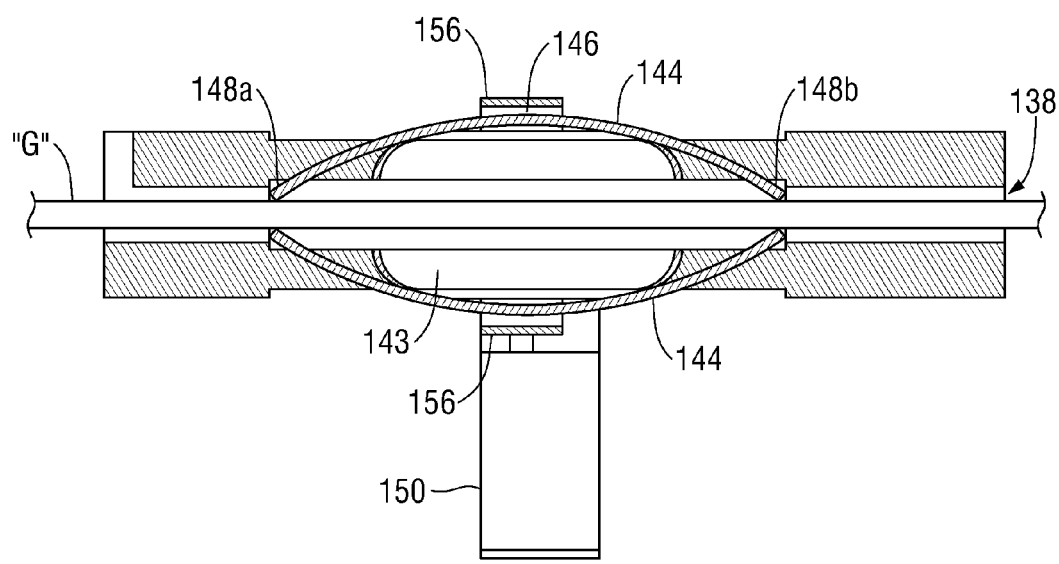
FIG. 6B is a cross-section view of the torque and gripper assembly and trigger member in an engaged position in accordance with an embodiment of the present disclosure.
Figure 6C:
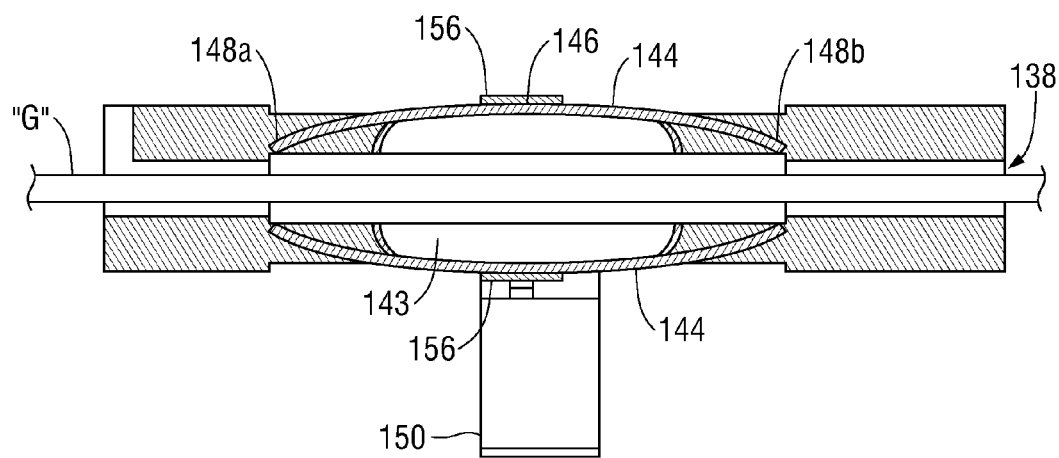
FIG. 6C is a cross-section view of the torque and gripper assembly and the trigger member in a released position in accordance with an embodiment of the present disclosure.

FIGS. 6A-6C illustrate the torque and gripper assembly 106 positioned within the resilient strap 156 of the trigger member 110. The resilient strap 156 is concentrically disposed about the central arc segments 146 of the leaf springs 144. As shown in FIG. 6B, the leaf springs 144 of the gripper member 134 are normally biased to an engaged position such that the ends 148a, 148b are positioned radially toward the lumen 138 and will prevent entry of a guidewire or engage the guidewire. When a clinician actuates the trigger member 110 by pressing the lever 150, the resilient strap 156 moves from the first larger diameter to the second smaller diameter thereby causing the midpoint 146 of the leaf springs 144 to move radially towards the central shaft segment 143. (FIG. 6C) Moving the central arc segment 146 of the leaf springs 144 toward the central shaft segment 143 causes the ends 148a, 148b of the leaf springs 144 to move radially away from the lumen 138 within the respective apertures 142a, 142b thereby permitting a guidewire to be positioned or repositioned within the lumen 138. Releasing the lever 150 causes the 148a, 148b of the leaf springs 144 to move radially toward the lumen 138 thereby securing a guidewire within the lumen 138. In other words, when the leaf springs 144 are in the engaged position, the leaf springs 144 have a first radius of curvature that causes ends 148a, 148b to engage the lumen 138 and any guidewire positioned therein. Upon actuation of the lever 150, the radius of curvature of the leaf springs 144 transition to a second radius of curvature that is greater than the first radius of curvature thereby moving ends 148a, 148b away from the lumen 138 and permitting a guidewire to be positioned or repositioned in the lumen 138. (FIG. 6C)

Figure 7:
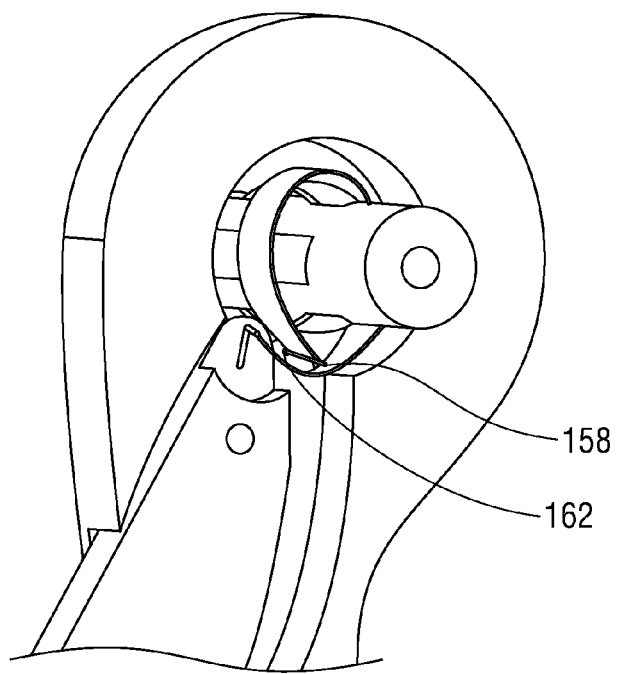
FIG. 7 is a perspective view of the torque and gripper assembly, trigger member, and the proximal handle segment in accordance with an embodiment of the present disclosure.

FIG. 7 illustrates the torque and gripper assembly 106 positioned within the resilient strap 156 of the trigger member 110 and the proximal handle segment 102a. As shown in FIG. 7, the first end 158 of resilient strap 156 is secured to the proximal handle segment 102a by inserting rod 158a (FIG. 5B) at the first end 158 into an aperture 162 of the proximal handle segment 102a. In the normal unstressed condition of the resilient strap 156, i.e., when the resilient strap 156 has the first larger diameter configuration, the resilient strap 156 biases the trigger in the initial position as shown in FIG. 7.

Figure 8:
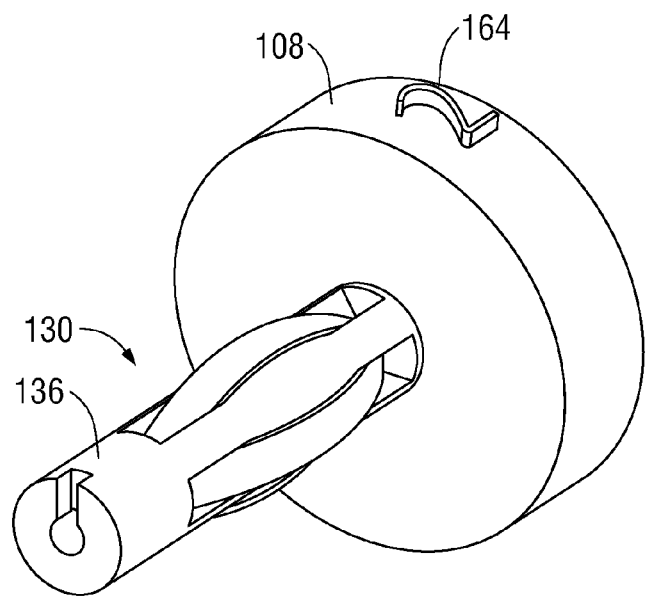
FIG. 8 is a perspective view of the torque member and the counter member in accordance with an embodiment of the present disclosure

Turning to FIG. 8, the counter member 108 circumscribes the shaft 136 near the distal end of the shaft 136. The counter member 108 is fabricated from any suitable material including polymeric materials formed by any conventional fabrication techniques known in the art. The counter number 108 includes indicia, in the form of, e.g., the numbers 164, that may indicate an incremental degree or number of rotations of the actuator 104 and the guidewire through a predetermined arc of rotation about the longitudinal axis "X". The numbers 164 may be any real number, e.g., integers ranging from . . . , −2, −1, 0, 1, 2, . . . where a negative number may indicate a counter clockwise direction and a positive number may indicate a clockwise direction or vice versa. The radius of the counter member 108 may be set to a predetermined length by the manufacturer. In other embodiments, the counter member 108 may be adjusted by a clinician to adjust the predetermined arc of rotation that is indicated by the numbers 164 by changing the radius of the counter member 108. The counter member may be frictionally fit over the shaft 136. Other methods of securing the counter member 108 to the shaft 136 are also contemplated that include, but are not limited to, a tongue and groove configuration, welding, etc.

In another embodiment, the shaft 136 may include a pair of ribs (not shown) at the distal end that are configured to secure the counter member 108 in the correct location so that the numbers 164 appear in the window 118.

In the embodiments described hereinabove, the actuator 104, the torque member 132 and the counter member 108 are described as being separate components. It is also contemplated that the actuator 104 and the torque member 132 may be formed as a unitary component, the torque member 132 and the counter member 108 may be formed as a unitary component, or that the actuator 104, the torque member 132, and the counter member 108 may be formed as a unitary component. Further, the handle member 102 was described hereinabove as being composed of two components (the proximal handle segment 102a and the distal handle segment 102b) that are separated along a plane that is transverse to the longitudinal axis "X". In other embodiments, the handle member 102 may be composed of two components that are separated along a plane that is aligned with the longitudinal axis "X". Also, the various components of the torque apparatus 100 may be assembled by a clinician or they may be preassembled by a manufacturer where the proximal handle segment 102a and the distal handle segment 110 may be welded together after assembly of the torque apparatus 100. Any of the components described herein may be disposable single use components or reposable.

Referring again to FIGS. 2 and 3, during use of the torque apparatus 100, the clinician grasps the torque apparatus 100 with a single hand. The clinician then actuates lever 150 with his/her index finger in order to introduce a guidewire through aperture 124, lumen 138, and aperture 116. The lever 150 is released and the guidewire is secured within the torque apparatus 100 by leaf springs 144, e.g., the ends 148a, 148b of the leaf springs 144. Then the clinician advances the guidewire in to a vessel by moving the torque apparatus 100 distally. While navigating the guidewire through the vessel, the clinician rotates actuator 104 with his/her thumb to orient the tip of the guidewire through the vasculature. When the clinician needs to reposition the torque apparatus 100 along the guidewire to increase the length of the guidewire available to be inserted into the vessel, the clinician actuates lever 150 and moves the torque apparatus 100 proximally before releasing the lever 150 to secure the guidewire in place. Once again, the torque apparatus 100 is moved distally to navigate the guidewire through the vessel. This procedure is repeated until the guidewire is located in the correct position within the vessel. After the guidewire is located in the correct position, the clinician actuates lever 150 and moves the torque apparatus 100 proximally over the guidewire until the guidewire is extricated.

Figure 9:
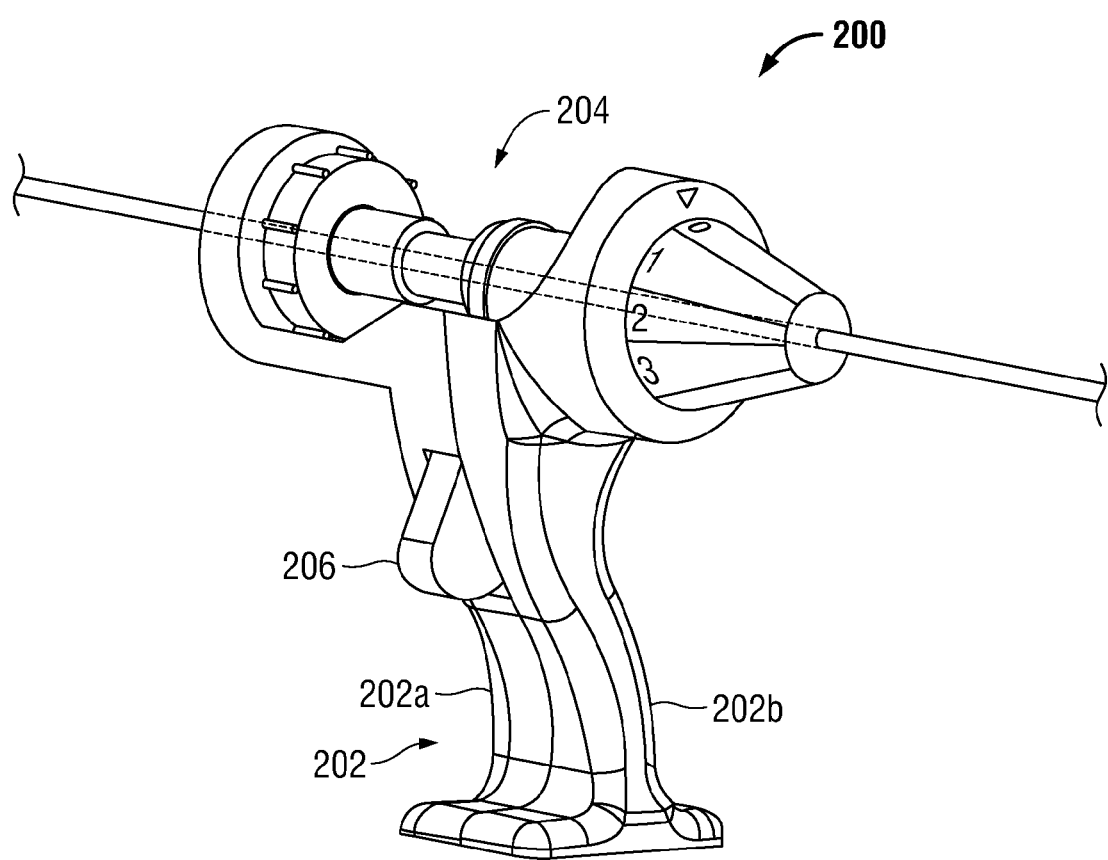
FIG. 9 is a perspective view of a torque apparatus in accordance with another embodiment of the present disclosure.
Figure 10:
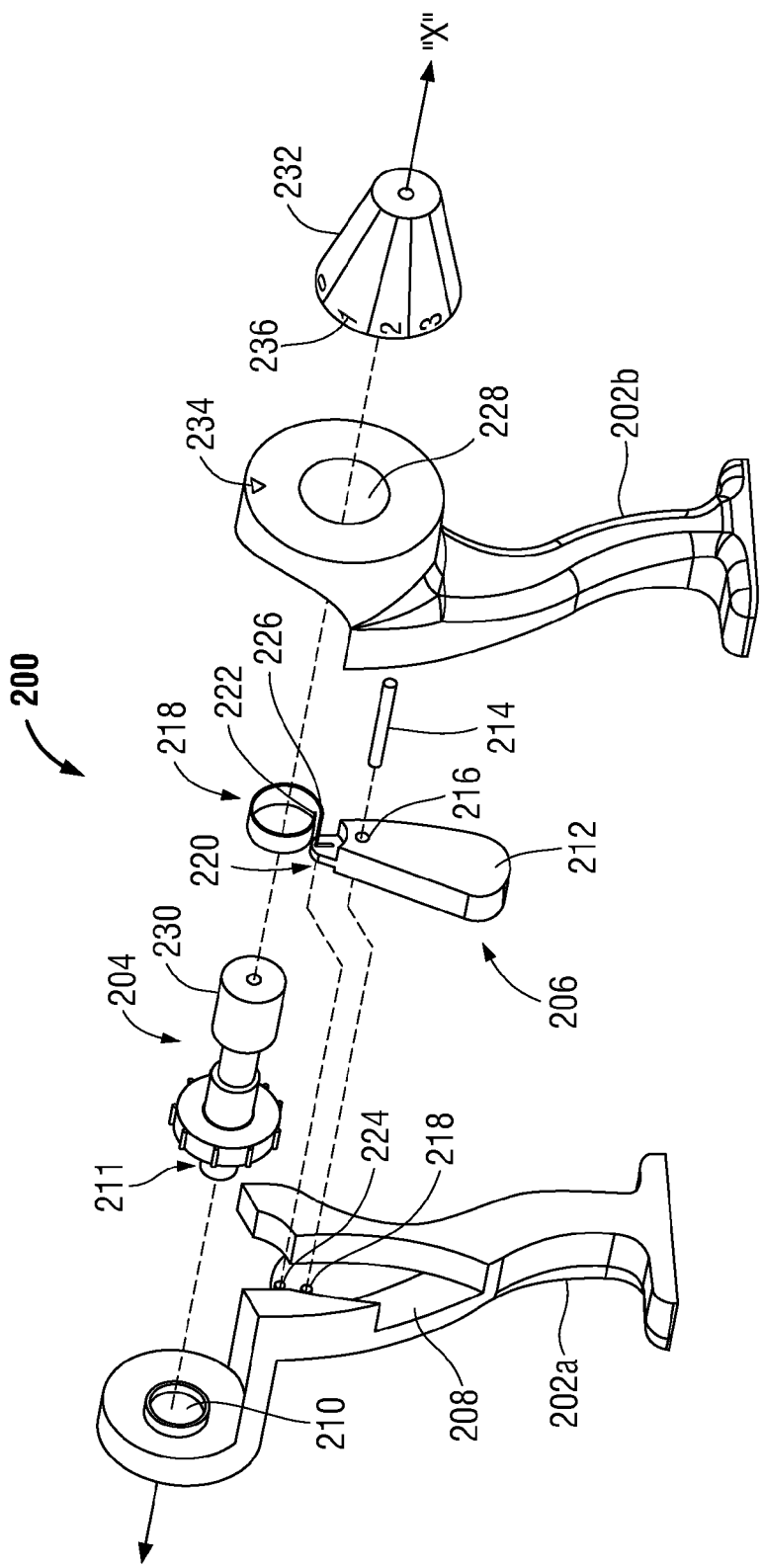
FIG. 10 is an exploded view of the torque apparatus of FIG. 9.

Referring now to FIGS. 9 and 10, a torque apparatus 200 in accordance with another embodiment of the present disclosure is illustrated. The torque apparatus 200 generally includes a handle member 202 and a torque and gripper assembly 204 positioned within the handle member 202. The torque apparatus 200 further includes a trigger member 206 depending from the handle member 202 and couplable to the torque and gripper assembly 204. The handle member 202 may be in the form of a pistol grip and defines a longitudinal axis "X". The handle member 202 has a substantially planar lower surface dimensioned to be positioned on a support or table in the upright orientation shown in FIG. 9.

The handle member 202 may include a proximal handle segment 202a and a distal handle segment 202b which are connected to each other by conventional means. The proximal handle segment 202a defines an internal recess 208 which at least partially accommodates the trigger member 206 and a recess 210 in general alignment with the longitudinal axis "X". The recess 210 at least partially accommodates a proximal end 211 of the torque and gripper assembly 204. The torque and gripper assembly 204 rotates freely about the longitudinal axis "X" within recess 210

The trigger member 206 includes a lever 212 which is pivotally mounted to the proximal handle segment 202a about pivot pin 214. In some embodiments, pivot pin 214 is inserted into aperture 216 of lever 212 and aperture 218 of proximal handle segment 202a to mount lever 212 to proximal handle segment 202a. The lever 212 is fabricated from any suitable material including polymeric materials formed by injection molding techniques.

The trigger member 206 further includes a resilient strap 218 having a first end 220 couplable to the proximal handle segment 202a. Specifically, the first end 220 is secured to the proximal handle segment 202a by inserting rod 222 at the first end 220 into an aperture 224 of the proximal handle segment 202a. The lever 212 is coupled to a second end 226 of the resilient strap 218. The resilient strap 218 has a generally circular configuration and may be fabricated from stainless steel, a shape memory alloy, or a polymeric material. Actuation through pivotal movement of the lever 212 from an initial position to a pivoted position about the pivot pin 214 causes the resilient strap 218 to transition from a first larger diameter to a second smaller diameter. For example, as a clinician actuates the lever 212, the lever 212 pivots about the pin 214 causing the second end 226 to move radially away from the longitudinal axis "X" while the first end 220 remains secured to the proximal handle segment 202a. This action causes the effective circumference of the resilient strap 218 to decrease. Upon release of the lever 212, the resilient strap 218 returns to the first larger diameter.

The distal handle segment 202b includes a central aperture 228 configured to receive a distal end 230 of the torque and gripper assembly 204. The distal end 230 of the torque and gripper assembly 204 is couplable to a cap 232 that is disposed distally of the distal handle segment 202b. The distal handle segment 202b may include an indicator, e.g., an arrow 234, which, in conjunction with the cap 232, indicates the number of torque increments applied to a guidewire inserted into the torque apparatus 200. Specifically, the cap 232 may have indicia, e.g., numbers 236, that are arranged circumferentially around the cap 232. The number 236 that is aligned with arrow 234 indicates the number of torque increments applied to the guidewire.

The proximal handle segment 202a and the distal handle segment 202b may be fabricated from any suitable material including polymeric materials formed by injection molding techniques, metallic materials such as stainless steel or any other suitable material. The handle segments 202a, 202b may be connected to each other by conventional means including adhesives, sonic welding techniques, fasteners or the like.

Referring now to FIGS. 11A-11B, the torque and gripper assembly 204 will be discussed. The torque and gripper assembly 204 includes a manual actuator 238 in the form of a wheel. The manual actuator 238 is disposed about a proximal washer 240 that is internally threaded. The distal end 230 of the torque and gripper assembly 204 includes a distal washer 242 having a washer 244 that extends proximally. The outer surface of the washer 244 is threaded and is configured to cooperate with the internal threads of proximal washer 240. As shown in FIG. 11B, the proximal washer 240 includes an annular chamber 246 configured and dimensioned to receive the washer 244 such that the proximal washer 240 may be positioned anywhere along the longitudinal length of the washer 244.

A gripper member 248 is disposed in a chamber 250 defined by the proximal washer 240, the distal washer 242 and the washer 244. Gripper member 248 acts as a valve and moves from a first engaged position in order to grip a guidewire inserted therein to a second release position to permit entry of or repositioning of a guidewire inserted therein. The gripper member 248 is a resilient material such as silicone, which is shapeable when subjected to compressive or tensive forces. The gripper member 248 maintains a constant volume. Thus, when one dimension of the gripper member changes, e.g., axial length, another dimension of the gripper member 248 changes, e.g., radial thickness, to maintain the volume of the gripper member 248. For example, in some embodiments, when the axial length of the gripper member 248 increases that radial thickness decreases and when the axial length of the gripper member decreases, the radial thickness of the gripper member 248 increases. A lumen 252 is aligned with longitudinal axis "X" of the handle 202 and is configured to receive the guidewire "G". Further details of the torque and gripper assembly 204 and their functioning in gripping and releasing the guidewire "g" will be discussed in greater detail hereinbelow.

During use of the torque apparatus 200, the clinician grasps the torque apparatus 200 with a single hand. The clinician then actuates lever 212 with his/her index finger causing resilient strap 218 to transition from a first larger diameter to a second smaller diameter. When the resilient strap 218 is in the second smaller diameter configuration, the resilient strap 218 frictionally engages the distal washer 242 of the torque and gripper assembly 204 preventing the torque and gripper assembly 204 from spinning. The clinician then rotates the manual actuator 238 in a first rotational direction causing the proximal washer 240 to move proximally. This action increases the axial length of the chamber 250 thereby permitting the gripper member 248 to assume its natural state having a first reduced thickness "$t_1$" as shown in FIG. 12A. After a guidewire is inserted into lumen 252 or repositioned within lumen 252, the manual actuator 238 is rotated in a second rotational direction opposite the first rotational direction thereby moving the proximal washer 240 distally along the longitudinal axis. This action reduces the axial length of the chamber 250 which applies a compressive force to the gripper member 248 in the axial direction thereby reducing the axial length of the gripper member 248. Reducing the axial length of the gripper member 248 increases the radial thickness of the gripper member to a second larger thickness "$t_2$" as shown in FIG. 12B. In the configuration shown in FIG. 12B, when the gripper member 248 assumes the configuration having the second larger thickness "$t_2$", the gripper member 248 frictionally engages the guidewire "G" inserted therein thereby preventing guidewire "G" from moving along the longitudinal axis "X". The clinician releases the lever 212 and advances the guidewire in to a vessel by moving the torque apparatus 200 distally. While navigating the guidewire through the vessel, the clinician rotates the manual actuator 238 with his/her thumb to orient the tip of the guidewire toward the appropriate path. When the clinician needs to reposition the torque apparatus 200 along the guidewire to increase the length of the guidewire available to be inserted into the vessel, the clinician actuates lever 212 and moves the manual actuator 238 in the first radial direction to release the guidewire before the torque apparatus 200 is moved proximally. After the guidewire is secured, the torque apparatus 200 is moved distally to navigate the guidewire through the vessel. This procedure is repeated until the guidewire is located in the correct position within the vessel. After the guidewire is located in the correct position, the clinician releases the guidewire and moves the torque apparatus 200 proximally over the guidewire until the guidewire is extricated.

The above description and the drawings are provided for the purpose of describing embodiments of the present disclosure and are not intended to limit the scope of the disclosure in any way. It will be apparent to those skilled in the art that various modifications and variations can be made without departing from the spirit or scope of the disclosure. Thus, it is intended that the present disclosure cover the modifications and variations of this disclosure provided they come within the scope of the appended claims and their equivalents.

What is claimed is:

1. A torque apparatus for manipulation of a guidewire, the torque apparatus comprising:
    a handle member dimensioned for engagement by a clinician and defining a longitudinal axis;
    a torque member mounted to the handle member and defining a lumen configured for reception and passage of a guidewire, the torque member being configured to rotate about the longitudinal axis and relative to the handle member to impart rotational movement to the guidewire;
    a gripper member associated with the torque member, the gripper member adapted to releasably secure the guidewire relative to the torque member;
    a trigger member depending from the handle member and operatively coupled to the gripper member, the trigger member actuable to cause the gripper member to release the guidewire to thereby permit the guidewire to move through the lumen of the torque member; and
    an actuator operatively coupled to the torque member, the actuator rotatable to impart rotational movement to the torque member to thereby cause corresponding rotational movement of the guidewire.

2. The torque apparatus according to claim 1, further comprising a counter member associated with the torque member, the counter member dimensioned and adapted to count incremental rotational movements of the torque member.

3. The torque apparatus according to claim 1 wherein the gripper member is movable between a first engaged position in engagement with the guidewire to substantially prevent movement of the guidewire through the lumen of the torque member and to operatively couple the guidewire to the torque member whereby rotational movement of the torque member causes corresponding rotational movement of the guidewire, and a second release position released from the guidewire to permit movement of the guidewire through the lumen.

4. The torque apparatus according to claim 3 wherein the gripper member is biased to the first engaged position.

5. The torque apparatus according to claim 3 wherein the trigger member is adapted for pivotal movement relative to the handle member between an initial position corresponding to the first engaged position of the gripper member and a pivoted position corresponding to the second release position of the gripper member.

6. The torque apparatus according to claim 5 wherein the trigger member is biased to the initial position.

7. The torque apparatus according to claim 6 wherein the torque member includes a shaft defining the lumen therethrough for reception of the guidewire and the gripper member includes at least one spring member mounted to the shaft, the at least one spring member arranged to engage the guidewire in general secured frictional relation therewith when the gripper member is the first engaged position and arranged to release the guidewire when the gripper member is in the second release position.

8. The torque apparatus according to claim 7 including a plurality of spring members extending in a general longitudinal direction with respect to the longitudinal axis.

9. The torque apparatus according to claim 1 wherein the handle member defines a substantially pistol grip arrangement.

10. The torque apparatus according to claim 1, wherein the actuator is concentric with the longitudinal axis.

11. A method comprising:
    actuating a trigger member of a torque apparatus to permit movement of a guidewire within a lumen of the torque apparatus, the trigger member being actuable by a finger on a first hand of a user, wherein the torque apparatus comprises:
        a handle member dimensioned for engagement by the user and defining a longitudinal axis;
        a torque member mounted to the handle member and defining the lumen configured for reception and passage of the guidewire, the torque member being configured to rotate about the longitudinal axis and relative to the handle member to impart rotational movement to the guidewire;
        a gripper member associated with the torque member, the gripper member adapted to releasably secure the guidewire relative to the torque member;
        the trigger member depending from the handle member and operatively coupled to the gripper member, the trigger member actuable to cause the gripper member to release the guidewire to thereby permit the guidewire to move through the lumen of the torque member; and
        an actuator operatively coupled to the torque member, the actuator rotatable to impart rotational movement to the torque member to thereby cause corresponding rotational movement of the guidewire;
    releasing the trigger member to secure the guidewire within the lumen of the torque apparatus;
    advancing the guidewire by moving the torque apparatus;
    torquing the guidewire by rotating the actuator of the torque apparatus, the actuator being rotatable by a thumb on the first hand of the user;
    actuating the trigger member to release the guidewire and permit movement of the guidewire within the lumen, the trigger member being actuable by the finger; and
    releasing the trigger member to secure the guidewire within the lumen of the torque apparatus.

12. The method according to claim 11 wherein the torque apparatus further comprises a counter member associated with the torque member, the counter member dimensioned and adapted to count incremental rotational movements of the torque member.

13. The method according to claim 11,
    wherein releasing the trigger member to secure the guidewire within the lumen of the torque apparatus comprises moving the gripper member to a first engaged position, in which the gripper member is in engagement with the guidewire to substantially prevent movement of the guidewire through the lumen of the torque member and operatively couples the guidewire to the torque member whereby rotational movement of the torque member causes corresponding rotational movement of the guidewire; and wherein actuating the trigger member to release the guidewire and permit movement of the guidewire within the lumen comprises moving the gripper member to a second release position released from the guidewire to permit movement of the guidewire through the lumen.

14. The method according to claim 13 wherein the gripper member is biased to the first engaged position.

15. The method according to claim 13, wherein moving the gripper member to the first engaged position comprises pivoting the trigger member relative to the handle member to an initial position corresponding to the first engaged position of the gripper member, and wherein moving the gripper member to the second release position comprises, moving the gripper member to a pivoted position corresponding to the second release position.

16. The method according to claim 15 wherein the trigger member is biased to the initial position.

17. The method according to claim 16 wherein the torque member includes a shaft defining the lumen therethrough for reception of the guidewire and the gripper member includes at least one spring member mounted to the shaft, the at least one spring member arranged to engage the guidewire in general secured frictional relation therewith when the gripper member is the first engaged position and arranged to release the guidewire when the gripper member is in the second release position.

18. The method according to claim 17 wherein the at least one spring member includes a plurality of spring members extending in a general longitudinal direction with respect to the longitudinal axis.

19. The method according to claim 11 wherein the handle member defines a substantially pistol grip arrangement.

20. The method according to claim 11 wherein the actuator is concentric with the longitudinal axis.

* * * * *